United States Patent
Weisbecker et al.

(10) Patent No.: US 11,614,404 B2
(45) Date of Patent: Mar. 28, 2023

(54) IN-LINE COATING WEIGHT AND RADIANT ENERGY EXPOSURE MEASUREMENT

(71) Applicant: Sun Chemical Corporation, Parsippany, NJ (US)

(72) Inventors: Carl S. Weisbecker, Jersey City, NJ (US); David Deshazer, Verona, NJ (US); Mohammad Farahat, Wyckoff, NJ (US)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 16/423,742

(22) Filed: May 28, 2019

(65) Prior Publication Data
US 2019/0310194 A1 Oct. 10, 2019

Related U.S. Application Data

(63) Continuation of application No. PCT/US2018/012919, filed on Jan. 9, 2018.
(Continued)

(51) Int. Cl.
*G01N 21/64* (2006.01)
*C09D 11/037* (2014.01)
(Continued)

(52) U.S. Cl.
CPC ....... *G01N 21/643* (2013.01); *B41F 23/0406* (2013.01); *C09D 11/037* (2013.01);
(Continued)

(58) Field of Classification Search
None
See application file for complete search history.

(56) References Cited

U.S. PATENT DOCUMENTS

| 3,076,723 A | 2/1963 | Covington |
| 4,250,382 A | 2/1981 | Libby |

(Continued)

FOREIGN PATENT DOCUMENTS

| DE | 3242489 A1 | 6/1984 |
| EP | 0 390 415 A1 | 10/1990 |

(Continued)

OTHER PUBLICATIONS

ASTM A754/A754M—11, Standard Test Method for Coating Weight (Mass) of Metallic Coating on Steel by X-Ray Fluorescence, 2016, 8 pgs.

(Continued)

*Primary Examiner* — Joshua D Zimmerman
(74) *Attorney, Agent, or Firm* — Frost Brown Todd LLP (57) ABSTRACT

A method for measuring the radiant exposure of energy curable inks or coatings on a printing press. The steps for measuring comprise: a) providing an ink or coating material comprising a fluorescent probe; b) transferring the ink or coating material onto a substrate using a printing process; c) exposing the ink or coating material to actinic radiation capable of initiating cure of the ink or coating material that also alters the luminescence of the probe; d) exposing the ink or coating to a first source of excitation light with wavelength and luminance capable of absorption by the fluorescent probe; and e) measuring the emitted light from the fluorescent probe by a first detector.

19 Claims, 6 Drawing Sheets

Related U.S. Application Data (60) Provisional application No. 62/444,408, filed on Jan. 10, 2017.

(51) Int. Cl.

| | |
|---|---|
| C09D 11/101 | (2014.01) |
| C09D 11/50 | (2014.01) |
| G01N 21/84 | (2006.01) |
| G01N 33/44 | (2006.01) |
| C09D 5/22 | (2006.01) |
| B41F 23/04 | (2006.01) |

(52) U.S. Cl.
CPC ............ *C09D 11/101* (2013.01); *C09D 11/50* (2013.01); *G01N 21/8422* (2013.01); *G01N 33/442* (2013.01); *C09D 5/22* (2013.01); *G01N 2021/8416* (2013.01); *G01N 2021/8427* (2013.01); *G01N 2201/08* (2013.01)

(56) References Cited

U.S. PATENT DOCUMENTS

| | | | |
|---|---|---|---|
| 4,651,011 A | 3/1987 | Ors et al. | |
| 4,956,558 A | 9/1990 | Batishko et al. | |
| 4,957,770 A | 9/1990 | Howarth | |
| 5,037,763 A | 8/1991 | Petisce | |
| 5,087,670 A | 2/1992 | Melancon et al. | |
| 5,100,802 A | 3/1992 | Mickols | |
| 5,270,116 A | 12/1993 | Melancon et al. | |
| 5,525,516 A | 6/1996 | Krutak et al. | |
| 5,574,288 A | 11/1996 | Harklau et al. | |
| 5,606,171 A | 2/1997 | Neckers et al. | |
| 5,717,217 A | 2/1998 | Neckers et al. | |
| 5,955,002 A | 9/1999 | Neckers et al. | |
| 5,968,479 A | 10/1999 | Ito et al. | |
| 6,410,926 B1 | 6/2002 | Munro et al. | |
| 6,534,041 B1 | 3/2003 | Licha et al. | |
| 7,043,326 B2 | 5/2006 | Neubauer et al. | |
| 7,079,262 B2 | 7/2006 | Jones et al. | |
| 7,242,747 B2 | 7/2007 | Zerle | |
| 7,329,630 B2 | 2/2008 | Gore | |
| 7,479,511 B2 | 1/2009 | Laksin et al. | |
| 7,612,122 B2 | 11/2009 | Herlihy et al. | |
| 8,350,064 B2 | 1/2013 | Strongin et al. | |
| 8,765,942 B2 | 7/2014 | Feraud et al. | |
| 8,927,052 B2 * | 1/2015 | Dubreuil | B05D 1/62 427/8 |
| 9,360,427 B2 | 6/2016 | Shukla | |
| 2010/0011656 A1 | 1/2010 | Gessner et al. | |
| 2012/0029108 A1 | 2/2012 | Nakane et al. | |
| 2016/0123881 A1 * | 5/2016 | Shukla | G01N 21/8422 436/2 |

FOREIGN PATENT DOCUMENTS

| | | |
|---|---|---|
| EP | 2 643 681 A2 | 10/2013 |
| JP | 2009-075002 A | 4/2009 |
| WO | WO 98/47538 A2 | 10/1998 |
| WO | WO 2012/071304 A2 | 5/2012 |

OTHER PUBLICATIONS

Barbero, N., et al., "Microwave-Assisted Synthesis of Near-Infrared Fluorescent Indole-Based Squaraines," Organic Letters, 2015, 17(13):3306-3309, 4 pgs.
Bunce, N.J. et al., "Solid State Actinometers Based on the Photorearrangement of Aromatic Azoxy Compounds in Poly(Methyl Methacrylate)," J. Photochem., 1986, 34(1):105:115, 11 pgs.
Buston, J.E.H., et al., "Rotaxane-encapsulated cyanine dyes: enhanced fluorescence efficiency and photostability," Chem Commun, 2000, 11:905-906, 2 pgs.
Caronna, T., et al., "Decomposition of a phthalocyanine dye in various conditions under UV or visible light irradiation," Journal of Photochemistry and Photobiology A: Chemistry, 2006, 184(1-2):135-140, 6 pgs.
Che, Y., et al., "Photoinduced dimerization of thymine in microemulsion for UVB radiation exposure measurements," Anal. Chim. Acta, 1995, 318(1):103-112, 10 pgs.
Cox, G., et al., "Measurement of thin coatings in the confocal microscope," Micron, 2001, 32(7):701-705, 5 pgs.
Decker, C., "Kinetic Study of Light-Induced Polymerization by Real-Time UV and IR Spectroscopy," Journal of Polymer Science Part A: Polymer Chemistry, 1992, 30(5):913-928, 16 pgs.
Falk, B., et al., "Optical Pyrometry: A New Method for Monitoring Photopolymerizations," RadTech el5 2004 Technical Proceedings, 12 pgs.
Fang, Y-F., et al., "Photocatalytic degradation of the dye sulforhodamine-B: A comparative study of different light sources," Journal of Environmental Sciences, 2007, 19(1):97-102, 6 pgs.
Flournoy, P.A., et al., "White-Light Interferometric Thickness Gauge," Appl. Opt., 1972, 11(9):1907-1915, 9 pgs.
Gróf, P., et al., "Use of Uracil Thin Layer for Measuring Biologically Effective UV Dose," Photochem. Photobiol., 1996, 64(5):800-806, 7 pgs.
Hageman, H.J., "Photoinitiators and Photocatalysts for Various Polymerization and Crosslinking Processes," *Radiation Curing of Polymers II*, D. R. Randell (ed.), Royal Society of Chemistry, 1991, pp. 46-60, 8 pgs.
Herlihy, S.L., "Factors influencing the efficiency of photoinitiation in radiation curable ink formulations," Ph.D. Thesis, University of Kent, England, 1997.
Herlihy, S., "The influence of UV light absorption and oxygen inhibition on photo DSC results," Proc. Radtech 1999, Berlin. [Reference unavailable].
ISO 9220:1988, Metallic Coatings—Measurement of Coating Thickness—Scanning Electron Microscope Method, Sep. 1988, 8 pgs.
Keeny, S.M., III, et al., "Fluorescent Cure Monitoring of Dental Resins," *Polymers of Biological and Biomedical Significance*, Chapter 18, ACS Symposium Series, Nov. 1993, 540:210-218, 9 pgs.
Khan, S.A., "In situ technique for monitoring the gelation of UV curable polymers," Rheol. Acta., 1992, 31(2):151-160, 10 pgs.
Lang, K., et al., "Photophysical properties of porphyrinoid sensitizers non-covalently bound to host molecules: models for photodynamic therapy," Coordination Chemistry Reviews, 2004, 248(3-4):321-350, 30 pgs.
Lapietra, B., "Cure measurement: an instrumental approach," Polymers Paint and Colour Journal, Oct. 1995, pp. 28-29. [Reference unavailable].
Li, H., et al., "Novel coumarin fluorescent dyes: Synthesis, structural characterization and recognition behavior towards Cu(II) and Ni(II)," Dyes and Pigments, 2011, 91(3):309-316, 8pgs.
Licha, K., et al., "Synthesis and characterization of cyanine dyes as contrast agents for near-infrared imaging," Proc. SPIE 2927, Optical and Imaging Techniques for Biomonitoring 11, 1996, pp. 192-198, 8 pgs.
May, R.K., et al., "Terahertz In-Line Sensor for Direct Coating thickness Measurement of Individual Tablets During Film Coating in Real-Time," J. Pharm. Sci., 2011, 100:1535-1544, 10 pgs.
Meier, H. "Photochemistry of Dyes," Chapter VII, *The Chemistry of Synthetic Dyes* Academic Press, Inc., 1971, pp. 389-515, 127 pgs.
Okabe, H., "Fading of quinoline dye by light: application to the measurement of the integrated lamp output and solar energy," Appl. Opt., 1981, 20(23):4054-4058, 5 pgs.
Pappas, S.P., ed., *Radiation Curing: Science and Technology*, Springer Science +Business Media, LLC (1992), Table of Contents Only, 9 pgs. Partial text available at https://books.google.com/books?hl=en&lr=&id=k0b2BwAAQBAJ&oi=fnd&pg=PA1&dq=electron+beam+radical+cure+mechanism&ots=ciNLoYC8SG&sig=WH6UGB391ZuQ42O6DYAAPrO4CP4#v=onepage&q&f=false.
Pitts, J.N., Jr., et al. "The Transfer and Conversion of Electronic Energy in Some 'Model' Photochemical Systems," Photochem. Photobiol., 1965, 4(3):305-321, 17 pgs.
Samanta, A., et al., "Development of photostable near-infrared cyanine dyes," Chem Commun, 2010, 46(39):7406-7408, 3 pgs.

(56) References Cited

OTHER PUBLICATIONS

Scherzer, T., et al., "Process Control of UV and EB Curing of Acrylates by In-line NIR Reflection Spectroscopy," RadTech e|5 2004 Technical Proceedings, 11 pgs.

Schrof, W., et al., "Characterization of Radiation Curable Coatings by Confocal Raman Spectroscopy," RadTech, 1998, North America, Conference Proceedings, 1998, p. 363-374. [Reference unavailable].

Seng, H.P., "ION Mobility Spectrometry, Controlling-Method for UV-Curing Processes: A Method for the End User," Proc. Radtech 95, Maastricht p. 101, 1 pg.

Skot, K., et al., "Scanning vibrating needle instrument for studying the kinetics of curing of oligomers," International Polymer Science and Technology, 1996, 23(10):T49-T52. [Reference unavailable].

Song, J.C., et al., "Characterization of Photocurable Coatings Using Fluorescence Probes," Polym. Eng. Sci., 1996, 36(3):394-402, 9 pgs.

Tathe, A.B., et al., "Novel Fluorescent Phenazines: Synthesis, Characterization, Photophysical Properties and DFT Calculations," J Fluoresc, 2015, 25(5):1403-1415, 13 pgs.

Zahouily, K., et al., "Real-time UV cure monitoring," European Coatings Journal, Vincentz Network, 2003, vol. 11, pp. 14, 10 pgs.

Zahouily, K., et al., "Cure Monitoring of UV-Curable Free Radical and Cationic Systems by Using In-situ Dielectric Analysis and Real-time FT-Infrared Spectroscopy," RadTech e|5 2004 Technical Proceedings, 8 pgs.

Zuo, X., et al. "Fluorescent Brighteners as Visible LED-Light Sensitive Photoinitiators for Free Radical Photopolymerizations," Macromolecular Rapid Communications, 2016, 37(10):840-844, 5 pgs.

International Search Report and Written Opinion dated Mar. 28, 2018 for Application No. PCT/US2018/012919, 17 pgs.

\* cited by examiner

IN-LINE COATING WEIGHT AND RADIANT ENERGY EXPOSURE MEASUREMENT

CROSS REFERENCE TO RELATED APPLICATIONS

The present application hereby claims the benefit of the provisional patent application titled "In-Line Coating Weight Monitor & Chemical Actinometer for Printed Energy Curable Material," Ser. No. 62/444,408, filed on Jan. 10, 2017, the disclosure of which is herein incorporated by reference in its entirety.

BACKGROUND

The performance of printed energy curable inks and coatings are affected by their coating weight and the curing by radiant energy exposure. Existing methods for measuring coating weight involves tedious, laborious, off-line procedures. Measurements involve taking periodic samples of the printed substrate. The ink or coating may be either stripped or dissolved from a measured, pre-weighed area of the substrate. The weight of the removed coating provides the coating weight. The shortcomings of this type of gravimetric method, particularly in a continuous operation, are immediately apparent. By the time one learns that the ink/coating weight is too low or too high, thousands of feet (at running rates of 100 yards/minute and higher) of coated substrate may have been run and wasted.

Likewise, off-line testing of the extent of the ink or coating cure by the radiant exposure takes time and thousands of feet of coated substrate would be wasted if the radiant exposure is not sufficient.

BRIEF SUMMARY

A method for measuring the radiant exposure of energy curable inks or coatings on a printing press. The steps for measuring comprise: a) providing an ink or coating material comprising a fluorescent probe; b) transferring the ink or coating material onto a substrate using a printing process; c) exposing the ink or coating material to actinic radiation capable of initiating cure of the ink or coating material that also alters the luminescence of the probe; d) exposing the ink or coating to a second source of excitation light with wavelength and luminance capable of absorption by the fluorescent probe; and e) measuring the emitted light from the fluorescent probe by a second detector.

The method may additionally comprise the steps, after step b) and prior to step c), of: 1) exposing the ink or coating to a first source of excitation light with a wavelength and luminance that is absorbed by the fluorescent probe but not capable of initiating cure in the ink or coating material; and 2) recording the emission of a fluorescent probe by a first detector.

The method may additionally comprise the steps, after step b) and prior to step c), of: 1) exposing the ink or coating to a second source of excitation light with a wavelength and luminance that is absorbed by the fluorescent probe but not capable of initiating cure in the ink or coating material; and 2) recording the emission of a fluorescent probe by a second detector.

These and other objects and advantages shall be made apparent from the accompanying drawings and the description thereof.

BRIEF DESCRIPTION OF THE FIGURES

The accompanying drawings, which are incorporated in and constitute a part of this specification, illustrate embodiments, and together with the general description given above, and the detailed description of the embodiments given below, serve to explain the principles of the present disclosure.

[1] Applicant does not intent to presently add "FIG. 3" to the specification. "FIG. 3" was already underlined in the specification.

[2] Applicant does not intent to presently add "FIG. 4" to the specification. "FIG. 3" was already underlined in the specification.

[3] Applicant does not intent to presently add "FIG. 5" to the specification. "FIG. 3" was already underlined in the specification.

[4] Applicant does not intent to presently add "FIG. 6" to the specification. "FIG. 3" was already underlined in the specification.

DETAILED DESCRIPTION

The radiant exposure of energy curable inks or coatings, and optionally their coating weight, can be continuously monitored in-line at high speed on a printing press using a fluorescent probe which is added to the ink or coating.

The method for measuring the radiant exposure of energy curable inks or coatings on a printing press comprises the steps of: a) providing an ink or coating material comprising a fluorescent probe; b) transferring the ink or coating material onto a substrate using a printing process; c) exposing the ink or coating material to actinic radiation capable of initiating cure of the ink or coating material that also alters the luminescence of the probe; d) exposing the ink or coating to a second source of excitation light with wavelength and luminance capable of absorption by the fluorescent probe; and e) measuring the emitted light from the fluorescent probe by a second detector. The light measured by the second detector may be correlated to the amount of actinic radiation exposure.

The method for measuring may additionally comprise the steps, after step b) and prior to step c), of: 1) exposing the ink or coating to a first source of excitation light with a wavelength and luminance that is absorbed by the fluorescent probe but not capable of initiating cure in the ink or coating material; 2) recording the emission of the fluorescent probe by a first detector. In some embodiments, the light measured by the first detector may be correlated to the coating weight of the energy curable ink or coating.

The problem of monitoring both the coating weight and the radiant exposure of a curable coating material exists in several industries. For example, curable materials are used in the manufacture of floor tiles, furniture, medical syringes, compact discs, computer floppy discs, video and audio tapes and glass fiber composites for automobiles and other products. These methods can be applied in many manufacturing printing processes.

The fluorescent probe changes its fluorescence properties after exposure to actinic radiation. In some embodiments, the fluorescent probe decomposes based on the amount of actinic radiation. It is believed that a highly reactive radical species is generated in situ by the actinic radiation, which reacts with the fluorescent probe to cause decomposition. The fluorescent probe is incorporated at a known concentration into the printable energy curable coating material.

In some embodiments, the fluorescent probe is a dye. Example decomposition processes are summarized in Schemes 1-3. Photo-oxidation at low concentrations of dye relative to oxygen content has been described in the most general terms as a D-O mechanism in which the dye (D), absorbing a photon (hv), enters an excited electronic state (D*). The D* state that interacts with oxygen will frequently be a triplet excited state ($^3$D*). The excited state of the dye reacts with oxygen to produce a semioxidized dye radical and a superoxide anion ($O_2$—.). The superoxide is a highly reactive species that could either react directly with the dye molecule to produce decomposition products or could react with a proton from its surroundings to form other reactive species able that could decompose the dye (Scheme 1). Note that the decomposition of the dye molecule involves reactions with photo-generated radical species in this scheme.

Scheme 1. UV light-induced decomposition of organic dye molecules under aerobic conditions.

$D+hv \rightarrow D^* \rightarrow {}^3D^*$ ${}^3D^*+O_2 \rightarrow D+.+O_2—.$ $O_2—.+H^+ \rightarrow HO_2.$ $2HO_2. \rightarrow H_2O_2+O_2$ $H_2O_2 \rightarrow 2OH.$ $D+O_2-. \rightarrow$ decomposition products $D+HO_2. \rightarrow$ decomposition products $D+OH. \rightarrow$ decomposition products It is widely known that the UV-light induced decomposition of dye molecules involving oxygen can be controlled or minimized in many instances by excluding oxygen by methods such as application of an oxygen barrier coating or performing UV light exposure under an inert atmosphere composed of nitrogen or other inert gas.

In the absence of oxygen, it is also expected that the UV light-induced or other actinic radiation induced decomposition of dye molecules involves reactions of the dye with generated radical species.

In the case of electron beam exposure, cure by a free radical mechanism typically occurs under an inert atmosphere, where nitrogen purge gas is used to exclude oxygen. Even when a photoinitiator is absent, fluorescent probes decompose by the electron beam generated radicals (Scheme 2). Unsaturated monomers (M) in the coating undergo inelastic collisions with e-beam electrons. The monomers enter an excited electronic state (M*) or form radical cations (M$^+$.). Several different radical species may be generated ($R_2$., $R_4$.). Some radicals react with additional monomer to initiate polymerization. Other radicals would be expected to react with dye molecules (D) leading to dye decomposition.

Scheme 2. Electron beam-induced decomposition of organic dye molecules under anaerobic conditions.

$M+e^- \rightarrow M^*+e^-$ $M+e^- \rightarrow M^+.+2e^-$ $M^* \rightarrow R_1+R_2.$ $R_2.+M \rightarrow RM. \rightarrow$ polymer $M^+. \rightarrow R_3^++R_4.$ $D+M^+. \rightarrow$ decomposition products $D+R_2. \rightarrow$ decomposition products $D+R_4. \rightarrow$ decomposition products Fluorescent probes may be used when the curing is initiated in the ink or coating by electron beam exposure and UV light exposure. These fluorescent probes work equally well whether the radiant exposure occurs under aerobic or anaerobic conditions.

Radical species are also generated in UV curable coatings in which polymerization of unsaturated monomers occurs by a free radical mechanism in the presence of a photoinitiator (P). Dye molecules are decomposed during free radical UV cure by reacting with UV light-generated radical species. The photoinitiator may be either a type I photoinitiator or a type 2 photoinitiator (Scheme 3). Fluorescent probes may be used in UV light curable inks or coatings that utilize both type 1 photoinitiators and/or type 2 photoinitiators to initiate a free radical cure mechanism.

Scheme 3. UV light-induced decomposition of organic dye molecules in the presence of photoinitiators.

$P+hv \rightarrow R_5.+R_6.$ (type 1 photoinitiator)

$R_6.+M \rightarrow RM. \rightarrow$ polymer $D+R. \rightarrow$ decomposition products or $P+hv \rightarrow P(type\ 2)^*$ (type 2 photoinitiator)

$P^*+R_7R_8N—CH_2—R_9$ (synergist)$\rightarrow HP.+R_7R_8N—CH.—R_9$ $R_7R_8N—CH.—R_9+M \rightarrow RM. \rightarrow$ polymer $D+R. \rightarrow b$ decomposition products Type 1 photoinitiators dissociate into radicals by a unimolecular process, mainly by α cleavage. Type 2 photoinitiators produce radical species by a bimolecular process involving hydrogen atom extraction from a synergist.

In some embodiments, the fluorescent probe is excited by light in a range of wavelengths between about 500 nm and about 1000 nm and emits light in a range of wavelengths between about 550 nm and about 1100 nm.

Example excitation ranges are between about 500 nm and about 1000 nm, such as about 520 nm and about 1000 nm, about 580 nm and about 1000 nm, about 600 nm and about 1000 nm, about 500 nm and about 900 nm, about 500 nm and about 800 nm, about 560 nm and about 900 nm, about 600 nm and about 900 nm, about 600 nm and about 800 nm, about 620 nm and about 800 nm, about 650 nm and about 800 nm, about 600 nm and about 750 nm, about 600 nm and about 700 nm, about 620 nm and about 700 nm, and about 650 nm and about 700 nm.

Example fluorescence light emission ranges are between about 650 nm and about 1000 nm, such as about 650 nm and about 900 nm, about 650 nm and about 800 nm, about 650 nm and about 750 nm, about 680 nm and about 1000 nm, about 680 nm and about 900 nm, about 680 nm and about 800 nm, and about 680 nm and about 700 nm. In addition, the fluorescence light emission may range from about 400 nm and about 550 nm.

The different excitation ranges and the emission ranges can be combined so long as the emission range is of equal or longer wavelength compared to the excitation range. It is to be understood that the examples are non-limiting, and other fluorescent probes with different absorption and emission characteristics could also be selected within the scope of this invention.

The fluorescence light emission range may be chosen so there is no unintended background fluorescence that may interfere with the measuring of the fluorescent probe. Many ink and coating materials of practical interest have some intrinsic fluorescence, and radiation curable inks or coatings often contain optical brighteners and other additives that may emit interfering light. Furthermore, some background substrate materials used in printing processes, especially some paper substrates, have intrinsic fluorescence which could interfere.

The fluorescent probe is present in the ink or coating material. In some embodiments, there is more than one fluorescent probe in the ink or coating material. In some embodiments, there is more than one ink or coating material and one or more of the ink or coating materials comprises a fluorescent probe. When there is more than one fluorescent probe present, they may be the same or different.

In some embodiments, the fluorescent probe is present in a range of about 1 to about 500 ppm of the coating composition, such as from about 1 ppm to about 100 ppm, about 1 ppm to about 50 ppm, and about 1 ppm to about 15 ppm.

Examples of fluorescent probes include, but are not limited to, cyanines, indocyanines, porphyrinoids, porphyrin derivatives and azaporphyrin derivatives, phthalocyanines, naphthalocyanines, xanthenes (including rhodamine derivatives and fluorescein derivatives), coumarin derivatives, phenothiazines, phenoxazines, phenazines, squaraines, croconic acid derivatives, triphenylmethane dyes, and rylene dyes. In some embodiments, the fluorescent probe is selected from phthalocyanine, phenothiazine, and cyanine. In some embodiments, the fluorescent probe is selected from phthalocyanine, and phenothiazine. In some embodiments, the fluorescent probe is selected from phthalocyanine and cyanine. In some embodiments, the fluorescent probe is selected from phenothiazine and cyanine. In some embodiments, the fluorescent probe is phthalocyanine. In some embodiments, the fluorescent probe is phenothiazine. In some embodiments, the fluorescent probe is cyanine.

In some embodiments, the fluorescent probe comprises a cyanine or indocyanine. Examples of cyanines include, but are not limited to the following: Cy5.5, Cy5 and Cy7 (Amersham, Arlington Hts., IL); IRD41 and IRD700 (LI-COR, Lincoln, Nebr.); NIR-1, (Dejindo, Kumamoto, Japan); LaJolla Blue (Diatron, Miami, Fla.); indocyanine green (ICG) and its analogs (U.S. Pat. No. 5,968,479, incorporated by reference in its entirety); indotricarbocyanine (U.S. Pat. No. 6,534,041, which is incorporated by reference in its entirety); cardiogreen, and 1,1'-diethyl-4,4'-carbocyanine iodide.

In some embodiments, the fluorescent probe comprises a porphyrinoid or phthalocyanine. Examples of porphyrinoids and phthalocyanine include, but are not limited to compounds described in Lang, K. (2004). Coordination Chemistry Reviews, 248(3-4), 321-350, such as: aluminum phthalocyanine, sulfonated aluminium phthalocyanine, 5,10-bis (N-methylpyridinium-4-yl)-15,20-bis(phenyl)porphyrin; 5,15-bis($\alpha$-triphenylphosphonium-4-tolyl)-10,20-bis(4-tolyl)porphyrin; hematoporphyrin; magnesium tetrakis(4-tert-butyl)phthalocyanine; magnesium tetrabenzoporphyrin; 5-(N-methylpyridinium-4-yl)-10,15,20-tris(phenyl)porphyrin; sulfonated metal-free phthalocyanine; palladium (II) 5,10,15,20-tetrakis(pentan-3-yl)porphyrin; palladium(II) 5,10,15,20-tetrakis(N-methylpyridinium-X-yl)porphyrin, X=2, 3 and 4; palladium(II) 5,10,15,20-tetraphenylporphyrin; palladium(II) 5,10,15,20-tetrakis(4-sulfonatophenyl) porphyrin; porphycene; protoporphyrin IX; 5,10,15,20-tetrakis($\alpha$-trimethylphosphonium-4-tolyl)porphyrin; 5,10,15,20-tetrakis(N-methylpyridinium-4-yl)porphyrin; 5,10,15,20-tetrakis(3,5-di-tert-butylphenyl)porphyrin; 5,10,15,20-tetrakis (4-carboxyphenyl)porphyrin; TPPP, 5,10,15,20-tetrakis(4-phosphonatophenyl)porphyrin; 5,10,15,20-tetrakis(4-sulfonatophenyl)porphyrin; 5,10,15-tris($\alpha$-triphenylphosphonium-4-tolyl)-20-(4-tolyl)-porphyrin; 2,7,12,17-tetra-n-propyl-porphycene; 5,10,15-tris(N-methylpyridinium-4-yl)-20-(phenyl)porphyrin; 5,10,15,20-tetrakis(4-tolyl)porphyrin; uroporphyrin I; zinc phthalocyanine; zinc tetrahydroxyphthalocyanine; sulfonated zinc phthalocyanine; zinc tetrabenzoporphyrin; zinc 5,10,15,20-tetrakis(2,6-dichloro-3-sulfonatophenyl)porphyrin; zinc 5,10,15,20-tetrakis(N-methylpyridinium-4-yl)porphyrin; zinc 5,10,15,20-tetrakis(4-sulfonatophenyl)porphyrin. In some embodiments, the porphyrin and phthalocyanine compounds comprise solubilizing groups such as sulfonate, quaternary ammonium, carboxylate and the like to improve the water solubility of these compounds.

In some embodiments, the fluorescent probe comprises metal-substituted fluorescent phthalocyanaines. Examples of metal-substituted phthalocyanines include, but are not limited to, aluminum phthalocyanines, zinc phthalocyanines, magnesium phthalocyanines, silicon phthalocyanines, and any fluorescent phthalocyanines substituted with the elements gallium, germanium, cadmium, scandium, or tin. In some embodiments, the fluorescent probe comprises fluorescent phthalocyanine substituted with the element phosphorus. In some embodiments, the phthalocyanine macrocycle is derivatized with solubilizing substituents such as sulfonic acid, phosphate, phosphonate, hydroxy, phenoxy, thiophenyl, amino, ammonium, or pyridinium groups.

In some embodiments, the fluorescent probe comprises a azaporphyrin derivatives, such as mono-, di- and triazaporphyrin and porphyrazine. Azaporphyrin derivatives may include, for example, phthalocyanine, benzotriazaporphyrin and naphthalocyanine derivatives. The preparation and fluorescent qualities of these dyes are known and many of these compounds are commercially available. These dye compounds act as multidentate macrocyclic ligands to chelate a central complexing atom. In some embodiments, the azaporphyrin fluorescent probe comprises a substantially planar multidentate macrocyclic ligand coordinated to a complexing central ion or atom, such as aluminum, phosphorous, and the group IVB elements, e.g. silicon, germanium and tin.

In some embodiments, the fluorescent probe comprises a xanthene, such as those described in U.S. Pat. No. 8,350,064, which is incorporated by reference in its entirety. Examples xanthene are rhodamines, such as tetramethylrhodamine, Rhodamine B, sulforhodamines, Texas Red, Rhodamine 101, Rhodamine 19, Rhodamine 110, and Carboxyrhodamine 6G. Other examples of xanthene include, but are not limited to, eosin, carboxyfluorescein, erythrosine, and Rose Bengal.

In some embodiments, the fluorescent probe comprises a coumarin, such as those described in *Dyes and Pigments*, 91(3), 309-316, Li, H. (2011). Examples include, but are not limited to: 1-benzopyran-2-one or benzoylhydrazonotrifluoroethyl)-7-(N,N-diethylamino)coumarin.

In some embodiments, the fluorescent probe comprises a phenothiazine, such as thionine, Methylene Blue, Methylene Green, Methylene Violet, and compounds described in U.S. Pat. No. 8,765,942, which is incorporated by reference in its entirety.

In some embodiments, the fluorescent probe comprises a phenoxazine, such as litmus, Nile Blue, and Nile Red, and Basic Blue 3.

In some embodiments, the fluorescent probe comprises a phenazine, such as those described in *Journal of Fluorescence*, 25(5), 1403-1415, Tathe, A. B. (2015). Examples include by are not limited to toluylene red.

In some embodiments, the fluorescent probe comprises a squaraine or croconic acid, such as those described in *Organic Letters*, 17(13), 3306-3309, Barbero, N., et al. (2015) and U.S. Pat. No. 5,525,516, which is incorporated by reference in its entirety.

In some embodiments, the fluorescent probe comprises a triphenylmethane dye, such as FD&C Blue 1, FD&C Green 3, Brilliant Green, Crystal Violet, Ethyl Violet, Victoria Blue R, Victoria Pure Blue BO, Victoria Blue B, and the like.

In some embodiments, the fluorescent probe comprises a rylene dye, such as perylene, terrylene, quarterrylene, and other poly(peri-naphthalene)s and their derivatives, also perylene diimide derivatives, and compounds described as markers for liquids in U.S. Publication 2010/0011656, which is incorporated by reference in its entirety.

In some embodiments, the fluorescent probe is capable of strong visible fluorescence in a range of wavelengths between 400 nm and 600 nm include fluorescent optical brighteners such as triazinylstilbene and 2,5-bis(5-tert-butyl-benzoxazol-2-yl)thiophene and fluorescent brightening agents described in U.S. Pat. No. 2012/0029108, which is incorporated by reference in its entirety.

In some embodiments, the fluorescent probe comprises a tetraphenylethylene, which are known to exhibit enhanced fluorescence in an aggregated state.

Any of a variety of radiation curable inks or coatings that comprise a fluorescent probe can be monitored for coating weight and radiant exposure. Such inks or coatings contain radiation curable materials that crosslink and/or polymerize by a free radical mechanism. In some embodiments, the ink or coating material is a is a UV or electron bean curable ink or coating material. Specific examples of actinic radiation curable materials include, but are not limited to, materials with unsaturated acrylate functional groups such as: silicon acrylates; urethane acrylates; epoxy acrylates; polyester acrylates; polyether acrylates. Examples of actinic radiation curable materials also include similar materials with unsaturated methacrylate groups. Examples include those disclosed in, U.S. Pat. Nos. 7,479,511 and 7,612,122, which are incorporated by reference in their entirety.

In some embodiments, the coating weight is from about 0.1 to about 300 lb./ream, such as about 0.1 to about 10 lb./ream, about 1 to about 10 lb./ream, about 1 to about 150 lb./ream, and about 30 to about 300 lb./ream. Coating weight may vary over a wide range that is dependent upon the coating method and the intended application for which the radiation curable coating will be used. Example 1 is a typical coating weight for an application to produce a gloss coating on paper using the method of flexographic printing for which the coating weight is expected to be broadly in a range of about 1 to about 10 lb./ream. In other types of applications, the coating may function as an energy curable primer to provide a desired surface property for adhesion. In such instances the desired coating weight may be as low as about 0.1 lb./ream. It should also be understood that coatings can be applied to substrates by other methods, such as spray coating, roll coating, slot die coating, screen printing, or curtain coating. Such other coating methods can apply higher coating weights. Screen printing is a printing process in which the coating is forced through a screen or stencil. Screen printing of UV/EB curable coatings may be used in applications such as for manufacturing printed circuit boards, membrane switches, backlit display panels, four color posters and irregularly shaped cosmetic containers. Coating weights up to about 150 lb./ream can be produced by screen printing. Curtain coating is a method that can also apply coating weight equivalent to about 30-300 lb./ream of coating weight.

In some embodiments, the ink or coating comprises monofunctional, difunctional, trifunctional, tetrafunctional, or multifunctional acrylate monomers or methacrylate analogs, such as, for example, one or more of: methyl methacrylate; lauryl acrylate; hydroxyethylmethacrylate; hydroxyethylacrylate; dipropylene glycol diacrylate; tripropylene glycol diacrylate; butanediol diacrylate; hexanediol diacrylate; alkoxylated hexanediol diacrylate; trimethyol propane triacrylate; alkoxylated trimethylol propane triacrylate; di(trimethylol propane triacrylate); glycerolpropoxy triacrylate; pentaerythritrol triacrylate; alkoxylated pentaerythritrol triacrylate; di(pentaerythritrol triacrylate); neopentaglycol diacrylate; alkoxylated neopentaglycol diacrylate; dipropylene glycol dimethacrylate; tripropylene glycol dimethacrylate; butanediol dimethacrylate; hexanediol dimethacrylate; alkoxylated hexanediol dimethacrylate; trimethyol propane trimethacrylate; alkoxylated trimethylol propane trimethacrylate; di(trimethylol propane methtriacrylate); glycerolpropoxy trimethacrylate; pentaerythritrol trimethacrylate; alkoxylated pentaerythritrol trimethacrylate; di(pentaerythritrol trimethacrylate); neopentaglycol dimethacrylate; alkoxylated neopentaglycoldimethacrylate.

In some embodiments, the ink or coating comprises materials with vinyl functional groups or vinyl ether functional groups. Examples of monomers that comprise vinyl functional groups include, 1-vinyl-2-pyrrolidinone, N-vinyl caprolactam, styrene, or styrene derivatives. In some embodiments, the ink or coating comprises other actinic radiation curable materials such as polyene—thiol compositions.

In some embodiments, the ink or coating is blended with organic or inorganic fillers or pigments, which are known to those skilled in the art of composite materials. Example inorganic fillers include, but are not limited to, ground quartz, fused silica, amorphous silica, talc, glass beads, graphite, carbon black, alumina, clays, mica, vermiculite, aluminum nitride, and boron nitride. A wide variety of organic and inorganic pigments may also be blended as is well known.

In some embodiments, the ink or coating comprises other additives, such as slip aids, flow aids, leveling agents, inhibitors, silicas, optical brighteners, cure accelerators, defoaming agents, deaerators, UV light stabilizers, anti-fade agents, UV absorbers, pigments, dyes, adhesion promoters, or resins. Examples of anti-fade agents are described in U.S. Pat. No. 7,329,630, which is incorporated by reference in its entirety In some embodiments, the ink or coating thickness is from about 0.05 to about 50 gsm (grams per square meter) dry, such as about 0.1 to about 20 gsm, and 0.1 to about 10 gsm.

In some embodiments, the inks or coatings are cured by ultraviolet light, and may comprise one or more photoinitiator. The selection of photoinitiators is well known to those of ordinary skilled in the art of radiation curing. Generally, for systems that cure via a radical mechanism, either Type 1 (cleavage) or Type 2 (H abstraction) radical photoinitiators may be used. In addition, small molecule, polymeric, or polymerizable photoinitiators may be used.

Any of a variety of substrates may be printed on or coated. Examples of substrates include, but are not limited to, most natural and synthetic polymeric films, such as polyethylene, polypropylene, polystyrene, PET, polyurethanes, epoxies; vinyl, such as PVC, polyamides and nylons; polyimides; elastomeric materials and rubbers; composites of materials; fiberglass as well as other materials, such as wood, particle board, glass, cement, ceramics, metals, cotton, wool, synthetic fibers, paper, other cellulosics, and virtually any structural material.

In some embodiments, the inks or coatings are printed onto substrates using a flexographic printing process. This printing process imposes constraints on physical properties of the ink or coating composition, because the composition must have rheological properties and chemical properties that are within the required parameters for flexographic printing. These requirements are generally known to those skilled in the art. The viscosity of the composition at 25° C. should be preferably within a range between 50 and 2000 cP at 100 s$^{-1}$. For flexographic printing the composition must adhere to the surfaces of the anilox roller and adhere to the surface of a flexographic plate that transfers a printed image to the substrate. The ingredients of the composition should be compatible with the plate material so not to cause swelling, distortion, or degradation of the plate material.

In some embodiments, the inks or coatings are printed onto substrates using other deposition methods such as gravure, lithographic offset, roll coating, spray coating, die coating, wicking, inkjet printing, or screen printing. The rheology of the coating composition's may need to be adjusted for proper deposition for a particular technique. This is well known to those skilled in the art. Coating thickness depends on the deposition technique used, but will generally be in the range of 0.5 to 10 gsm (grams per square meter) dry.

Actinic radiation is radiation that is capable of causing a chemical reaction in a substance. Either UV light or electron beams can be actinic. Curing in the sense of radiation-induced polymerization and chemical crosslinking are examples of such chemical reactions. In some embodiments, actinic radiation ranges from about 280 nm to about 420 nm. In some embodiments, the accelerating voltage of actinic electrons is in the range of 1 to 20 kV.

The coating on the substrate is exposed to actinic radiation capable of initiating cure in the coating material. This radiant exposure also alters the luminescence of the probe (radiation source in FIG. 1). In some embodiments, the fluorescent probe decomposes on exposure to the actinic radiation; the amount of decomposition is dependent upon the amount of actinic radiation.

After the actinic radiation exposure ends, the coating on the substrate is exposed to a first source of excitation light with wavelength λ3 and luminance L3 capable of absorption by the fluorescent probe. (Sensor 2 in FIG. 1). Emitted light from the fluorescent probe is recorded at wavelength λ4 and luminance L4. The measured luminance L4 is related to the amount of actinic radiation exposed to the coating.

Figure 2:
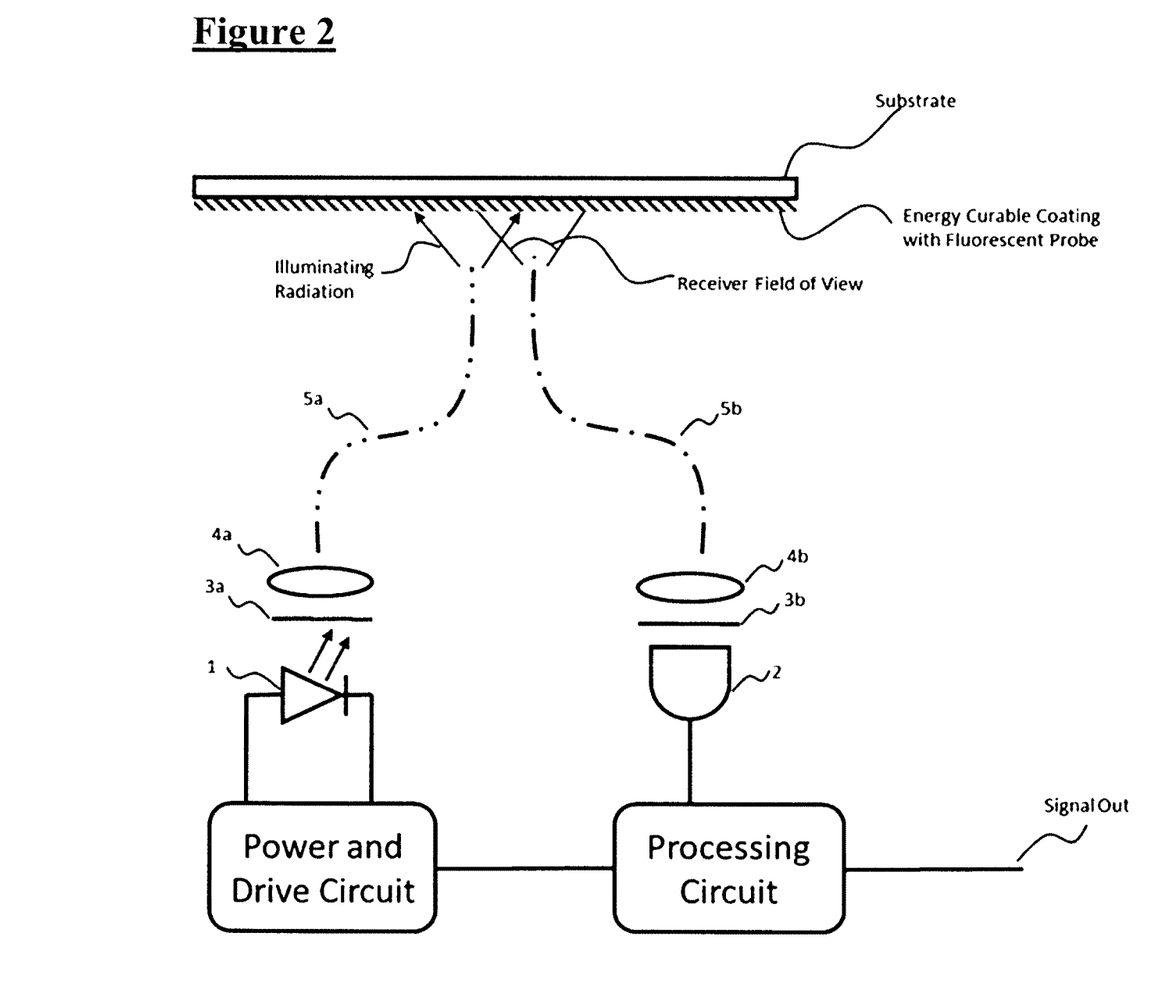
FIG. 2 is a schematic drawing of an embodiment of the components of an in-line sensor which emits excitation light and records a measured luminance.

FIG. 2 is a schematic drawing of the components of a sensor unit including of a source of excitation light, a fiber optic light guide, cut-off filters, and a photodetector. The numbered components in the drawing comprise (1) a light source, e.g. a light emitting diode; (2) a photodetector; (3a) a shortpass or bandpass filter; (3b) a longpass or bandpass filter; (4a and 4b) fiber optic coupling lenses; (5a) a fiber optic cable guiding excitation light toward the substrate; (5b) a fiber optic cable guiding emitted light from a fluorescent probe toward a photodetector.

Figure 1:
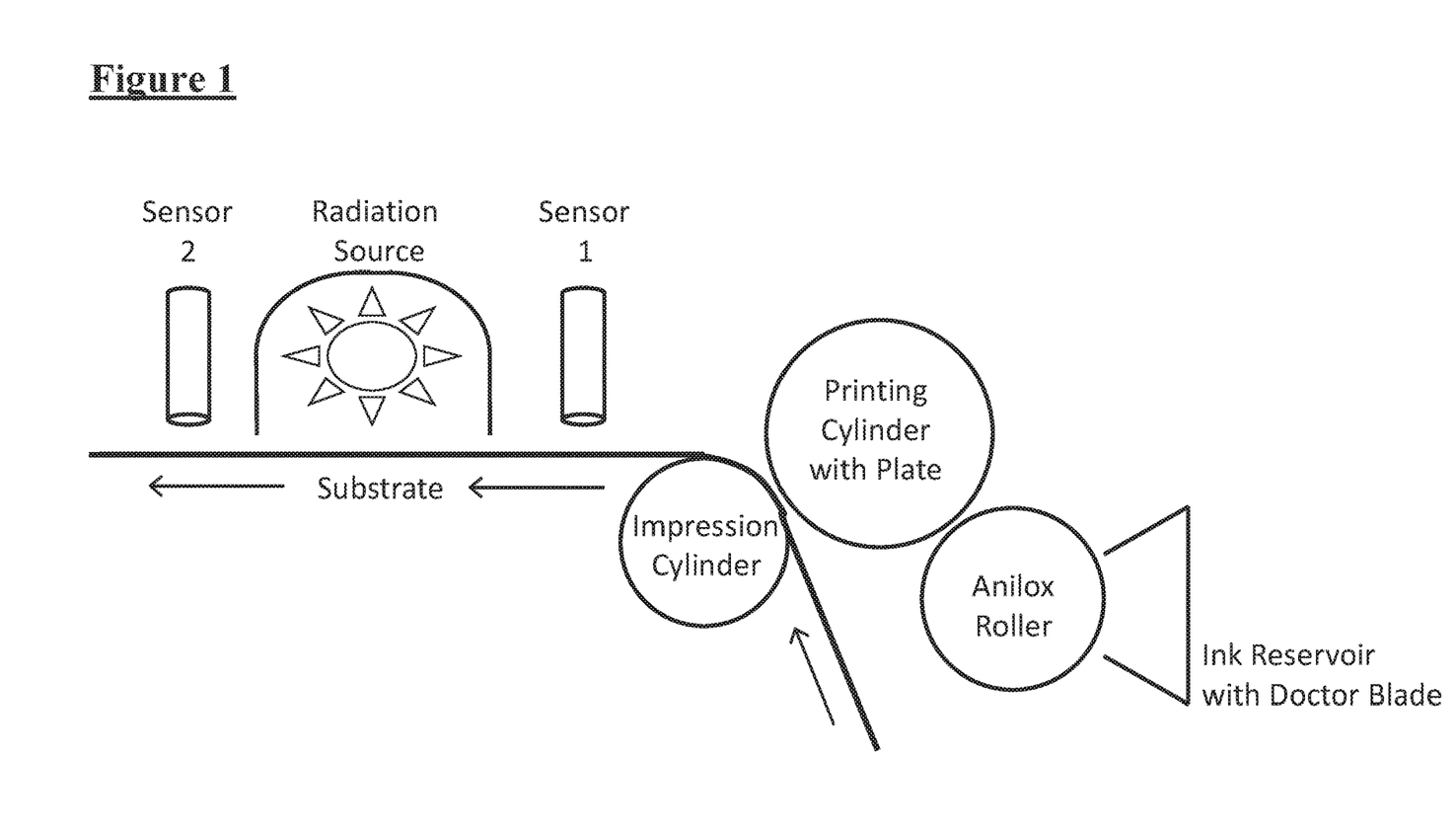
FIG. 1 is a schematic drawing of an embodiment of a printing process in which a coating is applied with a flexographic printing unit and cured by a radiation source on a continuous web substrate.

In some embodiments, prior to exposing the substrate to actinic radiation, it is exposed to a first source of excitation light with wavelength λ1 and luminance L1 capable of absorption by the fluorescent probe but not capable of initiating cure in the coating material (Sensor 1 in FIG. 1). Emitted light from the fluorescent probe at wavelength λ2 and luminance L2 is recorded. The measured luminance L2 of the probe is related to the coating weight on the substrate and serves as a coating weight monitor.

In some embodiments, the relationship between the two sensors is used to correlate the exposure of the substrate to actinic radiation. For example, the formula, C=(Sens1−m*Sens2)/Sens1−1, where m is a scale factor between the Sensor 1 and Sensor 2 that is empirically determined, may be used. In this case, no exposure would be when C=0, whereas C=1 would relate to complete quenching of the fluorescent probe. This is only one example of the relationship between the two Sensors, and others may be used.

The terms "first" and "second" sources of excitation light do not refer to the order of exposure, the "first" source of excitation light is exposed to the coating prior to the "second" source of excitation light. Sensor 2 comprises the second source and second detector. Sensor 1 comprises the first source and first detector.

FIG. 1 depicts a continuous process. It is based upon the nature of the substrate being printed; for example, a continuous long web fed from a roll. There are other printing processes in which the substrate is a stack of sheets or other items. The latter examples are discontinuous. An ink jet printing process can be continuous or discontinuous depending upon the nature of the substrate.

In some embodiments, the printing process is continuous. A continuous printing process is one that uses an unbroken substrate which is printed upon without the substrate stopping. The continuous printing process typically prints the same or a similar image at a regular interval upon the substrate. In some embodiments, the printing process is flexography.

The terms "energy curable" or "radiation curable" or "cured" as used herein, in reference to a printed material, means an ink or coating which can be cured, hardened, polymerized, or crosslinked by the action of actinic radiation such as UV or EB radiation and the like, or from a radiant energy source.

The term "radiant exposure" or "actinic radiation exposure" refers to an amount of actinic exposure experienced by a printed ink or coating layer on a substrate per unit area or per unit volume of the layer material. UV light exposure is often measured in units of mJ/cm² of the exposed layer surface. Electron beam exposure is often measured in units of kilograys, where a gray is defined as the absorption of one joule of ionizing radiation by one kilogram of matter.

The term "fluorescent probe" as used herein refers to a compound with a characteristic luminescence property, including fluorescence or phosphorescence, when excited by light, which is incorporated into an ink or coating in its liquid state unexposed to actinic radiation. The luminescence of the compound (1) increases with coating weight of the ink or coating in its unexposed liquid state and (2) decreases with increasing radiant exposure of the ink or coating. Alternately, the luminescence of the compound (1) increases with coating weight of the ink or coating in its unexposed liquid state and (2) increases with increasing radiant exposure of the ink or coating.

The term "ink" refers to printed colorant as used by ink jet printers, flexographic printers, etc. The term ink may include dye-based inks and/or pigment-based inks. Dye-based inks comprise a dye which may be an organic molecule which is soluble in the ink medium. Pigment-based dyes comprise a pigment, which is a solid colored particle suspended in the ink medium. The particle may comprise a colored mineral, a precipitated dye, a precipitated dye which is attached to a carrier particle, etc. Inks may be dispensed, deposited, sprayed, etc., on a substrate (e.g., ink-receptive layer) in the form of droplets which then dry on the substrate to form the printed image(s).

The term "coating" refers to a printed varnish or lacquer material that is lacking in visible color or pigmentation. Coatings may also be dispensed, deposited, sprayed, etc., on a substrate (e.g., ink-receptive layer) in the form of droplets which then dry on the substrate to form the printed image(s).

The term "coating weight" refers to an amount of a coating or ink present on a given side or surface of the paper substrate or layer being coated. Surface coverage may be defined in terms of grams (of solids) of the printable composition per square meter of paper substrate or layer.

The term "printable" refers to a material that can be applied selectively to form an image on a substrate having a print receptive surface.

The term "flexographic" (also referred to as "flexo") refers to a method of printing that uses a flexible relief plate. Flexographic methods also use a specially designed or engraved roller (anilox roller) having a surface containing a plurality of recessed dimples or cells for receiving and transferring the printable material to the substrate. Flexographic methods may use highly fluid printable materials (e.g., water-based inks), specially designed polymer relief printing plates, and light pressure in the printing nip area.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

Example 1

Step 1: Preparation of Energy Curable Coating Material with Fluorescent Probe

Probe 1 was added to a UV curable flexographic overprint varnish to produce a printable radiation curable material as shown in Table 1. This coating contains acrylate monomers and oligomers, a Type II photoinitiator, amine synergists, and other additives.

TABLE 1

Example 1 Formulation with 6.7 ppm of fluorescent probe

| Material | Type | Amount (wt. %) |
|---|---|---|
| Trimethylolpropane triacrylate | Acrylate Monomer | 49.41933 |
| Triethanolamine | Synergist | 3.00 |
| Methyldiethanolamine | Synergist | 3.00 |
| Ebecryl 9161 | Epoxy Acrylate Oligomer | 34.00 |
| Omnirad OMBB | Type II Photoinitiator | 9.00 |
| Irgacure 1173 | Photoinitiator | 1.00 |
| Erbeck One | Slip Agent | 0.18 |
| Foamtrol 110 | Antifoam | 0.10 |
| UV Inhibitor | Stabilizer | 0.20 |
| Optiblanc PL | Optical Brightener | 0.10 |
| ¹Probe 1 | Fluorescent Probe | 0.00067 |
| Total | | 100.00 |

¹Probe 1 is chloroaluminum phthalocyanine. Probe 1 was first blended into some finished UV coating product as a concentrate at 500 ppm using a lab mixer. This concentrate was then added to 12 kg of coating while blending on a Schold mixer. Mixing time was one hour. The temperature of the product was monitored and reached a maximum of 97° F.

A proof of the coating was made on paper stock with an 11.8 bcm anilox hand proofer, and luminance of the proof was measured. Additional Probe 1 was then added to adjust the product followed by additional mixing for another hour as before. A second proof was made, and luminance was measured. This resulting final level of Probe 1 was considered acceptable, having a signal approximately 10× the paper background.

Step 2: Preparation of Excitation Light Sources and Emitted Light Detection Assemblies Two sensors were positioned on a Ko-Pack UV flexographic printing press. Sensor 1 was located immediately upstream of the coating UV cure lamp. Sensor 2 was located several feet downstream of the lamp prior to a 90° turn. The sensors' height above the web was fixed at 0.190 in.

Step 3: Printing Press Set-Up and Operation

The Ko-Pack Press has multiple UV flexo printing units that are arranged around a central impression cylinder. The final printing unit was used to apply the exemplary UV flexographic overprint varnish.

The coating weight was controlled and varied by installing three different anilox rollers on the coating unit to provide high, medium, and low weights to the substrate. The substrate used was white paper with a basis weight of 100 gsm. The following anilox rollers were used:

120 line 16 bcm
180 line 10 bcm
220 line 8 bcm

The radiation exposure was controlled and varied in two ways. In the first way, the UV lamp power setting was adjusted among three different settings available: high, medium, and low lamp power. In the second way, the effective radiation exposure was altered for a given lamp setting by changing the press speed. The press was run at either a slow speed of 100 fpm or a fast speed of 400 fpm.

When running at the slow speed the radiation intensity was independently measure using UV Intensity Labels from UV Process Supply. These labels change from yellow to blue dependent on their level of exposure to UV light. The color change of labels, after passing under the lamp, was measured with a hand-held X-Rite Spectrophotometer (measuring $D_c$). The color change was related to a level of UV exposure as measured with a UV Power Puck Radiometer from EIT passed under a UV lamp in a laboratory. Results are summarized in Table 2. The total exposures indicate the UV maximum exposure experienced by the coating on press when the press is running at low speed for each lamp setting. When the press increases to its top speed, the exposure is correspondingly diminished by the shortened dwell time under the lamp. These independent measurements demonstrate the ability to control and vary the radiation exposure while measuring luminance from the in-line sensor.

TABLE 2

UV Exposure Levels on Press at Low Speed

| UV-A | UV-B | UV-C | UV-V | Total | $D_c$ |
|---|---|---|---|---|---|
| Lamp Setting - Low (mJ/cm²) | | | | | |
| 52 | 55 | 6 | 26 | 139 | 0.31 |
| Lamp Setting - Medium | | | | | |
| 104 | 101 | 12 | 52 | 269 | 0.45 |
| Lamp Setting - High | | | | | |
| 115 | 111 | 13 | 60 | 299 | 0.54 |

Table 3 summarizes results from various press trial treatments that consisted of different combinations of anilox roller, lamp power setting, and press speed. The following properties were measured of the printed materials: gravimetric coating weight, MEK double rub resistance, coating percent conversion by IR spectroscopy, and the coating extractables by GC.

Figure 3:
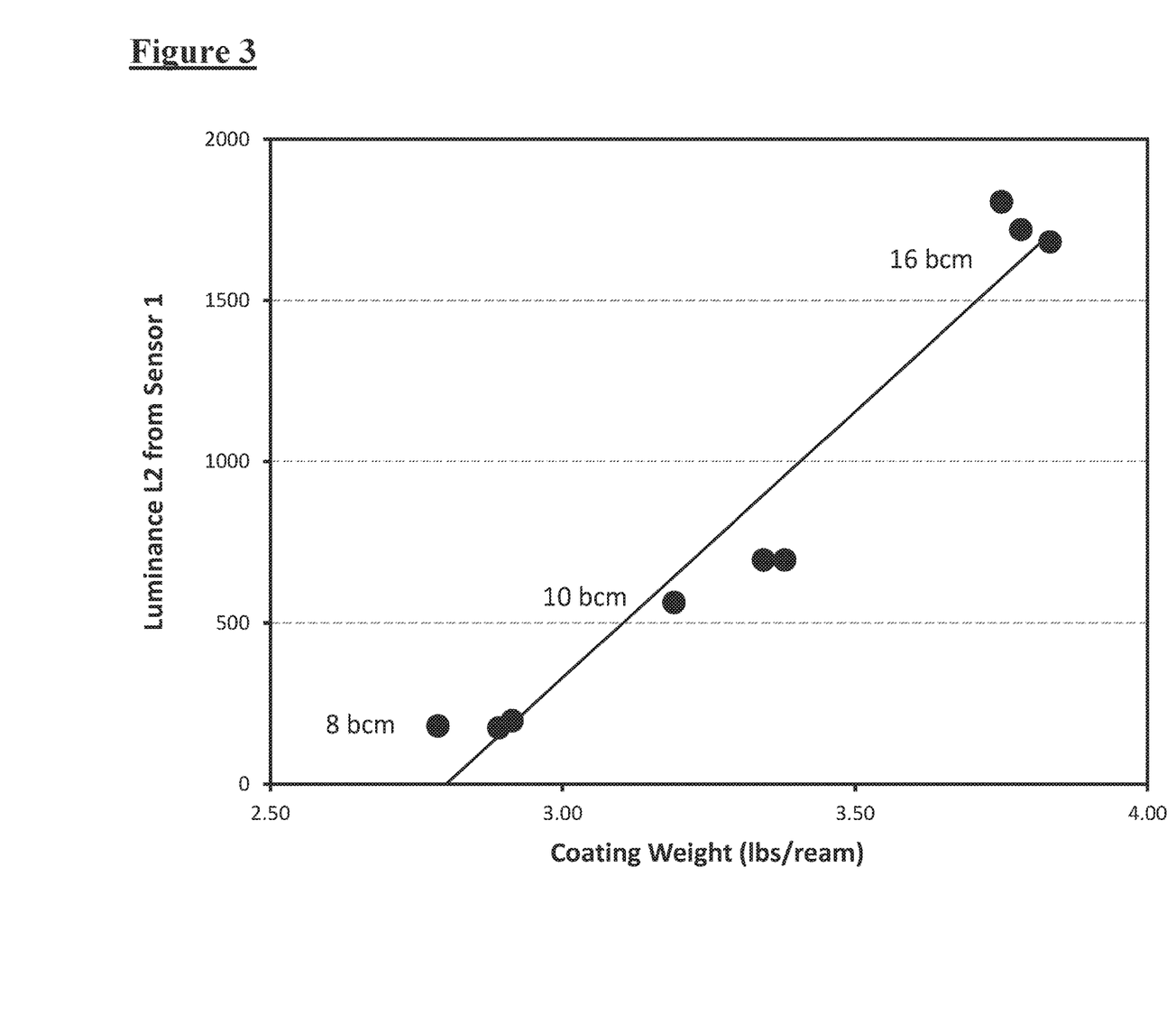
FIG. 3 is a plot showing an example relationship between off-line measured coating weight and in-line luminance (L2) measured by Sensor 1 (first source and first detector).
Figure 4:
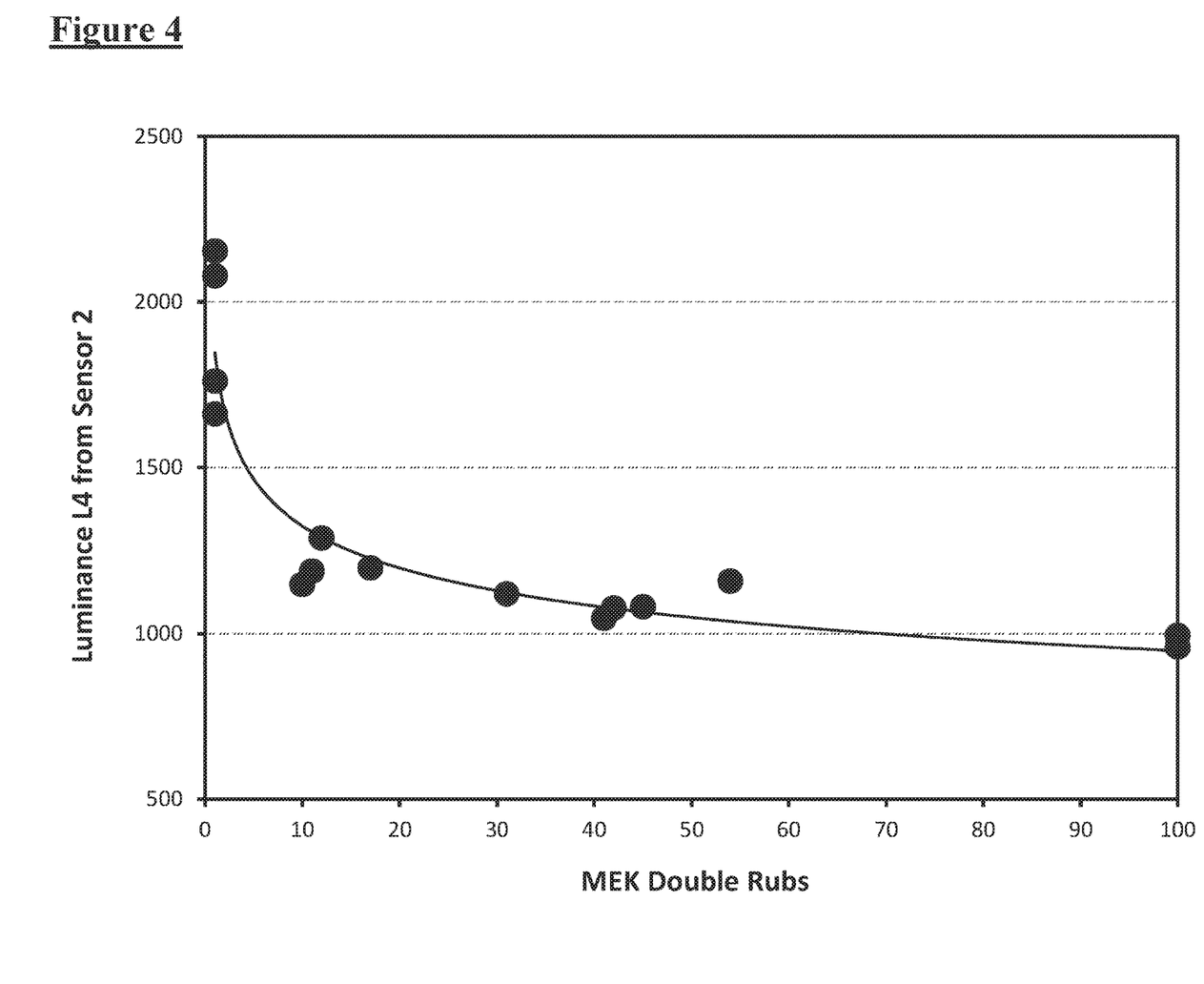
FIG. 4 is a plot showing an example relationship between double bond conversion as measured off-line by infrared spectroscopy and in-line luminance (L4) measured by Sensor 2 (second source and second detector).
Figure 5:
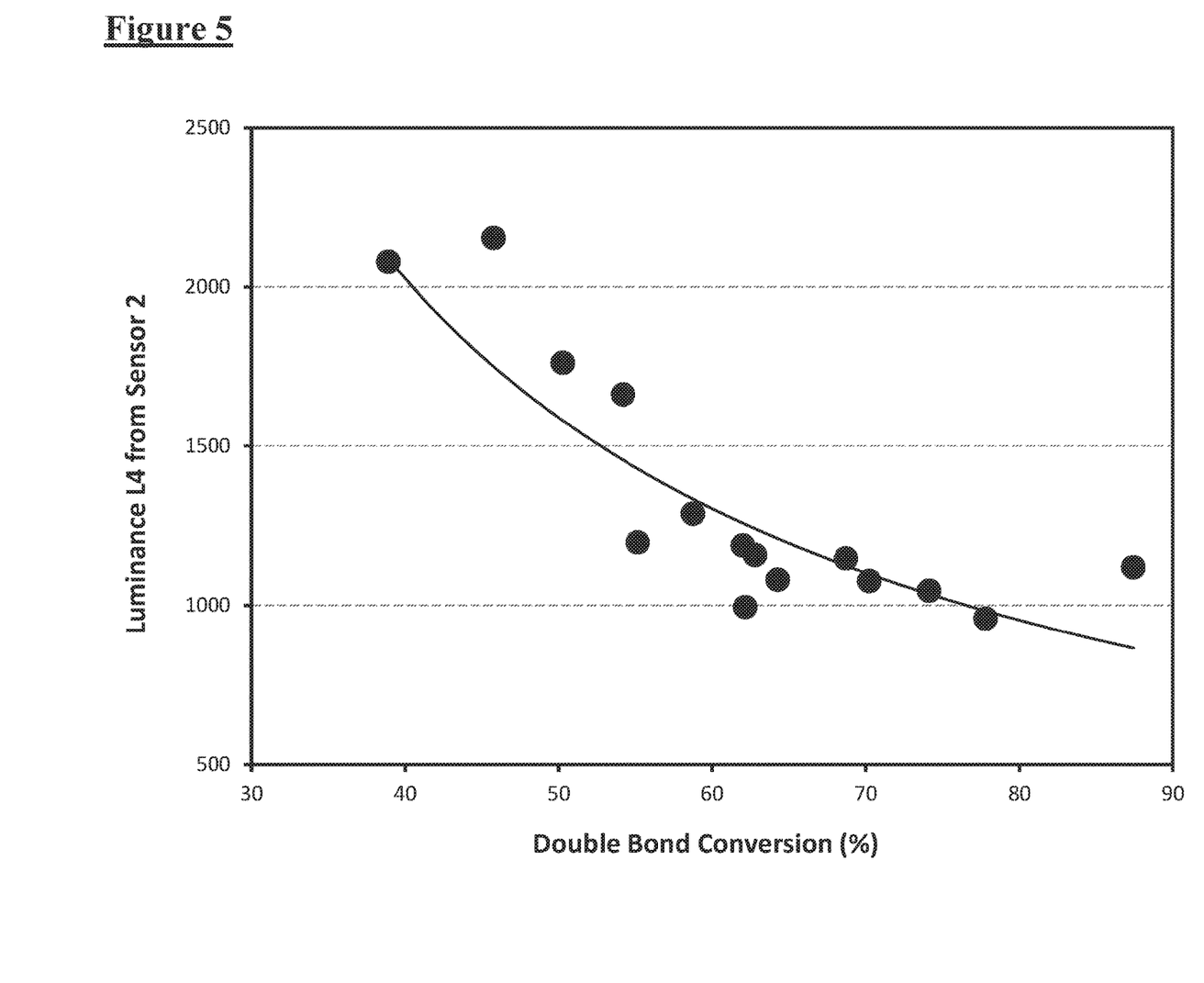
FIG. 5 is a plot showing an example relationship between off-line MEK double rubs of the coating surface and in-line luminance (L4) measured by Sensor 2 (second source and second detector).
Figure 6:
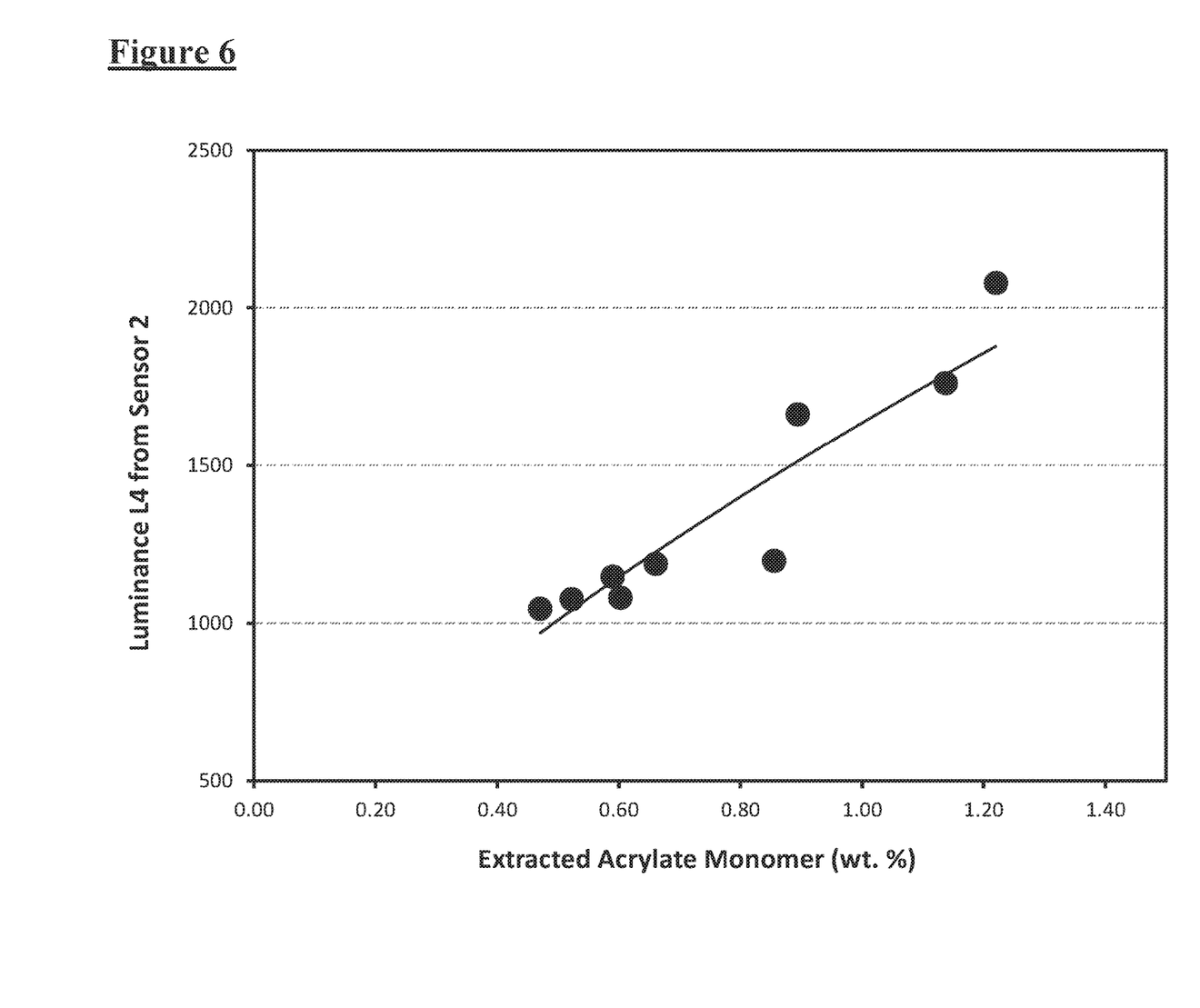
FIG. 6 is a plot showing an example relationship between extracted acrylate monomer determined by an analytical laboratory off-line and in-line luminance (L4) measured by Sensor 2 (second source and second detector).

The coating weights applied to paper using each anilox roller were measured off-line by a gravimetric method. Sheets of coated and uncoated paper were die cut into 2.5 in.×2.5 in. squares. Multiple squares were precisely weighed using an analytical balance, subtracting the weight of uncoated paper squares, to derive the weight of applied coating per unit area of the paper expressed in units of pounds per ream. The average coating weight thus obtained from each printing run was plotted in FIG. 3 versus the signal luminance (L2) from Sensor 1. In this example, the relationship between the off-line measured coating weight and the in-line Sensor 1 signal is a monotonically increasing function, i.e. it increases but not necessarily linearly, which establishes its capability to measure the applied coating weight.

Results of this testing are also summarized in Table 3 and FIGS. 3, 4, 5, and 6. Taken together, these results demonstrate that the signal recorded in real time by Sensor 1 was related to the UV coating weight as measured gravimetrically such that Sensor 1 acts as an in-line coating weight monitor. Also, these results demonstrate that the signal recorded by Sensor 2 was related to the radiation exposure of the coating. Radiation exposure of a printed UV coating is typically assessed indirectly by methods such as MEK double rub testing.

A UV coating is judged to be sufficiently cured by radiation exposure if the number of MEK double rubs required to scratch it exceeds a threshold value. The Sensor 2 signal varies inversely with MEK double rubs. Analytical tests such as double bond conversion by infrared spectroscopy and determination of extractable acrylate monomer are also used to assess if UV coating cure due to radiation exposure is sufficient. The signal recorded by Sensor 2 varies inversely with the double bond conversion and proportionally to the acrylate monomer extractables. Each of these relationships demonstrates that the luminance from Probe 1 detected by Sensor 2 acts as an in-line actinomer.

TABLE 3

Results from Press Trial Treatments of Prints

| Treatment | Anilox (bcm) | Lamp | Speed (fpm) | Coating Weight (lbs/ream) | Double Bond Conversion (%) | MEK Double Rubs | Extracted Monomer (%) | Sensor 1 | Sensor 2 |
|---|---|---|---|---|---|---|---|---|---|
| 1 | 16 | high | 400 | 3.75 | 64 | 45 | 0.60 | 1806 | 1080 |
| 2 | 16 | medium | 400 | 3.83 | 55 | 17 | 0.86 | 1681 | 1197 |
| 3 | 16 | low | 400 | 3.78 | 39 | 1 | 1.22 | 1719 | 2078 |
| 4 | 10 | high | 400 | 3.19 | 70 | 42 | 0.52 | 563 | 1076 |
| 5 | 10 | medium | 400 | 3.38 | 62 | 11 | 0.66 | 695 | 1187 |
| 6 | 10 | low | 400 | 3.34 | 50 | 1 | 1.14 | 695 | 1761 |
| 7 | 8 | high | 400 | 2.89 | 74 | 41 | 0.47 | 174 | 1045 |
| 8 | 8 | medium | 400 | 2.79 | 69 | 10 | 0.59 | 180 | 1147 |
| 9 | 8 | low | 400 | 2.91 | 54 | 1 | 0.89 | 196 | 1662 |
| A1 | 16 | high | 100 | | 78 | 100 | | | 958 |
| A2 | 16 | medium | 100 | | 62 | 100 | | | 994 |
| A3 | 16 | low | 100 | | 63 | 54 | | | 1157 |
| B1 | 16 | high | 400 | | 87 | 31 | | | 1119 |
| B2 | 16 | medium | 400 | | 59 | 12 | | | 1287 |
| B3 | 16 | low | 400 | | 46 | 1 | | | 2153 |

Examples 2-5

Step 1: Preparation of Energy Curable Coating Material with Fluorescent Probe

Probe 2 was added to an energy curable flexographic overprint varnish to produce printable radiation curable materials as shown in Examples 2, 3, 4, and 5.

TABLE 4

Examples 2-5 Formulations with 12 ppm of fluorescent probe

| Material | Type | Amount (wt. %) | | | |
|---|---|---|---|---|---|
| | | Ex. 2 | Ex. 3 | Ex. 4 | Ex. 5 |
| Laromer LR 8765 | Acrylate Resin | 98.76 | 94.76 | 94.76 | 94.76 |
| Water | Diluent | 0.2388 | 0.2388 | 0.2388 | 0.2388 |
| Omnirad BDK | Type I Photoinitiator | — | 4 | — | — |
| Omnirad TPO-L | Type I Photoinitiator | — | — | 4 | — |
| Michler's Ethyl Ketone | Type II Photoinitiator | — | — | — | 4 |
| ICM 1042 | Leveling Agent | 1 | 1 | 1 | 1 |
| [2]Probe 2 | Fluorescent Probe | 0.0012 | 0.0012 | 0.0012 | 0.0012 |
| | Total | 100 | 100 | 100 | 100 |

[2]Probe 2 is methylene blue. Probe 2 was first dissolved in water to make a solution 0.5 wt. %. This aqueous dye concentrate was then blended together with other ingredients on a laboratory mixer.

Example 2 is curable by electron beam exposure but not by UV light exposure, because it contains acrylate resin but no photoinitiator. Examples 3 and 4 are UV curable compositions that each contain a Type I photoinitiator. Example 5 is a UV curable composition that contains a Type II photoinitiator, Michler's Ethyl Ketone, which is combined in the same molecule with an amine synergist.

The photoinitiators were first blended into acrylate resin using a laboratory mixer prior to blending in the marker and other ingredients. Mild heating was applied in a 50° C. oven to aid dispersal of solid photoinitiators in the resin.

Step 2: Preparation of Coatings and UV Light Exposure

Proofs of each coating were made on white polypropylene label stock using a 14.8 bcm anilox hand proofer. Luminance of each proof was measured using a hand-held near-infrared fluorescence monitor. The proofs were exposed to ultraviolet light by passing them at a speed of 200 fpm under a 400 wpi H-bulb mercury lamp. Proofs were passed repeatedly under the lamp, their luminance was measured again at different cumulative UV exposures. The UV exposure was measured using a UV Power Puck from EIT.

TABLE 5

Luminance of Proofs after Different Levels of UV Light Exposure

| UV Exposure (mJ/cm2) | Amount (wt. %) | | | |
|---|---|---|---|---|
| | Ex. 2 | Ex. 3 | Ex. 4 | Ex. 5 |
| 0 (unexposed proof) | 518 (wet) | 743 (wet) | 620 (wet) | 353 (wet) |
| 199 | 163 (wet) | 62 (dry) | 146 (dry) | 199 (wet) |
| 398 | 93 (wet) | — | — | 153 (wet) |
| 597 | 79 (wet) | — | — | 125 (dry) |
| 796 | 69 (wet) | — | — | — |
| 995 | 55 (wet) | — | — | — |

The results in Table 5 demonstrate that the luminance measured from Probe 2 in every coating is highest in the unexposed proof. Exposure to UV light results in a reduction of the measured luminance. The unexposed proofs were wet to touch. The proofs required different cumulative amounts of UV light exposure to cure them to a dry tack-free state.

The proof of Example 2 remained wet throughout because no photoinitiator was added, and the luminance of Probe 2 diminished continuously, demonstrating that the change in luminance of the probe is affected by the radiation exposure, not by the extent of curing of the acrylate resin.

Proofs of Examples 3-4 each were exposed to UV light and cured to a dry, tack-free state within a single pass through the curing unit. The luminance of Probe 2 also diminished from that of the unexposed state.

The proof of Example 5 is representative of a composition that cured poorly and required an excessive level of exposure to achieve a dry tack-free state. The luminance of the probe also diminished with increasing exposure until the coating became fully cured after three passes through the curing unit.

Examples 6 and 7

Step 1: Preparation of an Electron Beam Curable Coating Material with Fluorescent Probe Probe 3 and Probe 2 were each added to energy curable flexographic overprint varnishes to produce printable e-beam curable materials Examples 6 and 7, respectively. Table 6 shows the composition of Example 6. Example 7 has the same composition as that of Example 2 above. Neither example contains a photoinitiator.

TABLE 6

Example 6 Formulation with 2.4 ppm of fluorescent probe

| Material | Type | Amount (wt. %) |
|---|---|---|
| Laromer LR 8765 | Acrylate Resin | 98.952 |
| Water | Diluent | 0.04776 |
| ICM 1042 | Leveling Agent | 1 |
| [3]Probe 3 | Fluorescent Probe | 0.00024 |
| | Total | 100 |

[3]Probe 3 is diethyl carbocyanine. Probe 3 was first dissolved in water to make a solution 0.5 wt. %. This aqueous dye concentrate was then blended together with other ingredients on a laboratory mixer.

Step 2: Preparation of Coatings and UV Light Exposure

Proofs of each coating were made on white polypropylene label stock. Example 7 was proofed using a 14.8 bcm anilox hand proofer. Example 6 was proofed using a 5.0 bcm anilox hand proofer. Luminance of each proof was measured using a near-infrared fiber-optic detector with an excitation wavelength of 670 nm. The proofs were exposed to actinic radiation by passing them at a speed of 15 meters per minute under an electron bean emitter with a voltage of 100 kV and surface dose of 30 kGy. Proofs were exposed under a nitrogen purge with ≤30 ppm oxygen.

TABLE 7

Luminance of Proofs after Different Levels of Electron Beam Exposure

| E-Beam Surface Dose (kGy) | Ex. 7 | Ex. 6 |
| --- | --- | --- |
| 0 (unexposed proof) | 2595 (wet) | 740 (wet) |
| 30 | 202 (dry) | 159 (dry) |

The results in Table 7 demonstrate that the luminance measured from either Probe 2 or Probe 3 is highest in the unexposed proof. Exposure to the electron beam results in a reduction of the measured luminance. The unexposed proofs were wet to touch. The electron beam exposed proofs cured to a dry tack-free state.

Examples 8-12

Examples 1-7 comprise from 2.3-12 ppm of fluorescent probe. Examples 1-7 were formulated for use in coatings that have a typical printed coating weight in the range of 1-10 lb./ream, but it is understood that the compositions could comprise a much broader ppm range of fluorescent probe for use in applications that may require a thinner or thicker coating weight based on end use requirements. In some embodiments, the probe is present in a range of 1-500 ppm of the coating composition. Examples with the probe in this range are summarized in Table 8.

TABLE 8

Examples 8-12 Formulations with 20-500 ppm of fluorescent probe

| | | Amount (wt. %) | | | | |
| --- | --- | --- | --- | --- | --- | --- |
| Material | Type | Ex. 8 | Ex. 9 | Ex. 10 | Ex. 11 | Ex. 12 |
| Ethoxylated trimethylolpropane triacrylate | Acrylate Monomer | 58.198 | 58.195 | 58.19 | 58.18 | 58.15 |
| Ebecryl 7100 | Acrylate Oligomer | 13 | 13 | 13 | 13 | 13 |
| Dipentaerythritol pentaacrylate | Acrylate Monomer | 18 | 18 | 18 | 18 | 18 |
| BYK-UV 3575 | Surface Additive | 1 | 1 | 1 | 1 | 1 |
| BYK A 535 | Defoamer | 1 | 1 | 1 | 1 | 1 |
| UV Inhibitor | Stabilizer | 0.3 | 0.3 | 0.3 | 0.3 | 0.3 |
| Chivacure 70 | Photoinitiator | 7 | 7 | 7 | 7 | 7 |
| Resiflow LG-99 | Flow Control Additive | 1.5 | 1.5 | 1.5 | 1.5 | 1.5 |
| Probe 1 | Fluorescent Probe | 0.002 | 0.005 | 0.010 | 0.020 | 0.050 |
| Total | | 100 | 100 | 100 | 100 | 100 |

Proofs of the coatings of Examples 8-12 were made on white paper stock with an 9.2 bcm anilox hand proofer, and luminance of the proofs was measured before and after UV exposure. Proofs were exposed in an Innovation Machines cure unit using a mercury H-bulb lamp at 300 watts per inch while traveling at 8 fpm on a conveyor.

TABLE 9

Luminance of Proofs with Different Probe Levels before and after UV Exposure

| UV Exposure | Amount (wt. %) | | | | |
| --- | --- | --- | --- | --- | --- |
| (mJ/cm2) | Ex. 8 | Ex. 9 | Ex. 10 | Ex. 11 | Ex. 12 |
| Probe 3 Level (ppm) | 20 | 50 | 100 | 200 | 500 |
| 0 (unexposed proof) | 521 (wet) | 1062 (wet) | 1931 (wet) | 3243 (wet) | 4085 (wet) |
| 188 | 254 (dry) | 456 (dry) | 870 (dry) | 1521 (dry) | 2962 (dry) |

Those skilled in the art having the benefit of the teachings of the present invention as hereinabove set forth, can effect numerous modifications thereto. These modifications are to be construed as being encompassed within the scope of the present invention as set forth in the appended claims.

The invention claimed is:

1. A method for measuring a radiant exposure of energy curable inks or coatings on a printing press, the method comprising the steps of:
   a) providing an ink or coating material comprising at least one fluorescent probe;
   b) transferring the ink or coating material onto a substrate using a printing process;
   b') exposing the ink or coating material to a first source of excitation light with a wavelength and luminance that is absorbed by the at least one fluorescent probe but is not capable of initiating cure in the ink or coating material;
   b") recording an emission of the at least one fluorescent probe by a first detector;
   c) exposing the ink or coating material to actinic radiation capable of initiating cure of the ink or coating material and that also alters a luminescence of the at least one fluorescent probe;
   d) exposing the ink or coating material to a second source of excitation light with a wavelength and luminance capable of absorption by the at least one fluorescent probe, wherein the second source of excitation light has a wavelength between 500 nm and 1000 nm;
   e) measuring an emitted light from the at least one fluorescent probe by a second detector, wherein the at least one fluorescent probe comprises a dye selected from phthalocyanine, phenothiazine, and cyanine; and
   f) determining a coating weight of the ink or coating material based on the emission recorded by the first detector.

2. The method of claim 1, wherein the emitted light measured by the second detector is correlated to an amount of actinic radiation exposure.

3. The method of claim 1, wherein the printing process is continuous.

4. The method of claim 1, wherein the ink comprises more than one fluorescent probe.

5. The method of claim 1, wherein the printing process comprises providing more than one ink or coating material, wherein at least one of the more than one ink or coating material comprises a fluorescent probe.

6. The method of claim 1, wherein the ink or coating material is a UV or electron beam curable ink or coating material.

7. The method of claim 1, wherein the printing process is flexography.

8. The method of claim 1, wherein the actinic radiation is in a form of UV light or an electron beam.

9. The method of claim 1, wherein the at least one fluorescent probe has a peak fluorescence between 550 nm and 1100 nm.

10. The method of claim 1, wherein during step c) the luminescence of the at least one fluorescent probe is altered by a chemical change initiated by the actinic radiation exposure.

11. The method of claim 1, wherein the second excitation light has a wavelength of approximately 600-750 nm.

12. The method of claim 1, wherein the first excitation light has a wavelength of approximately 600-750 nm.

13. The method of claim 1, wherein the first or second excitation light is delivered from its source to the printed substrate using a fiber optic cable.

14. The method of claim 1, wherein the emitted light from the at least one fluorescent probe is delivered to the first or second detector using a fiber optic cable.

15. The method of claim 1, wherein the ink or coating material comprises 1-500 ppm of the at least one fluorescent probe.

16. The method of claim 1, wherein the ink or coating material comprises 1-250 ppm of the at least one fluorescent probe.

17. A method for measuring a radiant exposure of energy curable inks or coatings on a printing press comprising:
   a) providing an ink or coating material comprising more than one fluorescent probe;
   b) transferring the ink or coating material onto a substrate using a printing process;
   b') exposing the ink or coating material to a first source of excitation light with a wavelength and luminance that is absorbed by the at least one fluorescent probe, but that is not capable of initiating cure in the ink or coating material;
   b") recording an emission of the at least one fluorescent probe using a first detector;
   c) exposing the ink or coating material to actinic radiation capable of initiating cure of the ink or coating material that also alters a luminescence of the at least one fluorescent probe;
   d) exposing the ink or coating material to a second source of excitation light having a wavelength of between 500 nm and 1000 nm; and
   e) measuring an emitted light from the at least one fluorescent probe by a second detector.

18. The method of claim 17, wherein an emitted light measured by the first detector is correlated to a coating weight of the ink or coating material.

19. A method for measuring a radiant exposure of energy curable inks or coatings on a printing press comprising:
   a) providing an ink or coating comprising at least one fluorescent probe selected from:
   phthalocyanine, phenothiazine, and cyanine;
   b) transferring the ink or coating onto a substrate using a printing process;
   c) exposing the ink or coating to a first source of excitation light with a wavelength and luminance that is absorbed by a fluorescent probe, but that is not capable of initiating cure in the ink or coating;
   d) measuring an emitted light of the at least one fluorescent probe with a first detector;
   e) exposing the ink or coating to actinic radiation capable of initiating cure of the ink or coating that also alters a luminescence of the at least one fluorescent probe;
   f) exposing the ink or coating to a second source of excitation light with a wavelength and luminance capable of absorption by the at least one fluorescent probe;
   g) measuring emitted light from the at least one fluorescent probe by a second detector; and
   h) correlating an emission of the at least one fluorescent probe measured with the first detector with a coating weight of the ink or coating.

* * * * *